United States Patent [19]

Bore et al.

[11] Patent Number: 4,948,876
[45] Date of Patent: Aug. 14, 1990

[54] KERATIN POLYMER CONTAINING S-SULPHOCYSTEINE RESIDUES, PROCESS FOR ITS PREPARATION AND THE COMPOSITIONS CONTAINING IT

[75] Inventors: Pierre M. Bore, Montfermeil; Jean-Claude Arnaud, Paris, both of France

[73] Assignee: "L'Oreal", Paris, France

[21] Appl. No.: 218,220

[22] Filed: Jul. 13, 1988

Related U.S. Application Data

[60] Division of Ser. No. 836,068, Mar. 4, 1986, abandoned, which is a continuation of Ser. No. 467,371, Feb. 17, 1983, abandoned.

[30] Foreign Application Priority Data

Feb. 17, 1982 [FR] France ................................. 82 02606

[51] Int. Cl.$^5$ ...................... C07K 15/20; A61K 37/12
[52] U.S. Cl. ...................... 530/357; 424/70; 424/71; 424/72; 435/68.1; 514/773
[58] Field of Search ................... 530/357; 435/69; 514/773; 424/70, 71, 72

[56] References Cited

U.S. PATENT DOCUMENTS

4,349,470  9/1982  Battista ................................. 514/773
4,390,525  6/1983  Yoshioka et al. ................... 514/773

FOREIGN PATENT DOCUMENTS

1503640 12/1967 France .
2061956  5/1981 United Kingdom .

OTHER PUBLICATIONS

Preis de Mycologie, Langerson, Masson et cie, Editors (1952), pp. 520–587 (chapter XVIII).
Chem–Abstracts, vol. 77 (1972), 149555, Kunert.
Chem–Abstracts, vol. 84 (1976), 176466e, Kunert.
Zeitschrift, Für Allg. Mikrobiologie, 13, 1973, pp. 489–498, Kunert.

*Primary Examiner*—Howard E. Schain
*Attorney, Agent, or Firm*—Cushman, Darby & Cushman

[57] ABSTRACT

A novel keratinic polymeric product is described which can be used for cosmetic purposes. This product comprises keratin peptide chains of different molecular weights, formed of amino acids bonded to one another by amide groups with more than 75 percent of the cystine linkages being in the form of S-sulphocysteine, the said peptide chains terminating at one end in a free carboxyl group and at their other end in a free amine group, the major part of said chains having a molecular weight of 1,100 to 7,500.

5 Claims, No Drawings

KERATIN POLYMER CONTAINING S-SULPHOCYSTEINE RESIDUES, PROCESS FOR ITS PREPARATION AND THE COMPOSITIONS CONTAINING IT

This is a division of Application Ser. No. 06/836,068, filed Mar. 4, 1986, now abandoned, which is a continuation of Ser. No. 06/467,371 filed Feb. 17, 1983, now abandoned.

The present invention relates to a new polymer derived from kerain and containing S-sulphocysteine groups, which can be prepared by an enzymatic digestion process.

It is known that keratin polymers are of great value in the cosmetic industry for their action of the surface condition of hair. They can be prepared by the acid or alkaline chemical hydrolysis, or preferably by the enzymatic digestion, of keratin substances. The function of the chemical or enzymatic hydrolysis is to split the long peptide chains of the keratin into water-soluble peptides of lower molecular weight. This gives mixtures of peptides of different lengths, which can contain a considerable amount of free amino acids, the peptide sequences being composed of amino acids joined to one another by amide groups and terminating at one end in a carboxyl group and at the other end in an amine group. The constituent amino acids of the peptide sequences are those of which the starting keratin is composed.

The starting keratin can have a variety of origins: it can be derived, in particular, from human hair, wool, bristles, for example pig's bristles, animal hair, poultry feathers and horn. It is observed that the efficiency of the enzymatic digestion of keratin using proteolytic or keratolytic enzymes is extremely low or even zero. Thus, with the aim of improving the efficiency of enzymatic digestion, it has already been proposed to carry out a sensitising treatment prior to enzymatic digestion. The efficiency of the enzymatic digestion is then substantially improved since it can be as high as 95% in some cases.

An object of the present invention is to provide a keratin polymer of novel structure, having particularly valuable characteristics in the field of hair treatment, which polymer can be prepared by enzymatic digestion having a very high efficiency.

The present invention provides a keratin polymer consisting of a statistical mixture of peptide chains of different molecular weights, derived from keratin substances and formed of amino acids bonded to one another by amide groups, the abovementioned peptide chains terminating at one end in a free carboxyl group and at their other end in a free amine group, characterised in that the peptide chains of the polymer have more than about 75 per cent of their cystine linkages in the form of S-sulphocysteine, the major part of the said chains having a molecular weight between about 1,100 and about 7,500. Preferably, the major part of the peptide chains has a molecular weight between 1,300 to 4,000. The peptides of this major part having an average molecular weight between about 1,300 and about 4,000 consist of chains containing from 12 to 35 amino acids. The major part may preferably represent more than 55 per cent of the chains.

Another important characteristic of the keratin polymer according to the invention is that it has an amino acid composition, both qualitative and quantitive, which is substantially identical to that of the keratin substances from which it was prepared. By way of example, the quantitative amino acid analysis of a typical hair is compared below with that of a polymer according to the invention, prepared in accordance with the procedure of Example 1 described below. The analysis is carried out be chromatography on an ion exchange resin, after acid hydrolysis of the keratin. The results of this analysis are expressed in mols of each amino acid per 100 g of total protein substance.

| COMPOSITION | TYPICAL HAIR | KERATIN POLYMER ACCORDING TO THE INVENTION |
| --- | --- | --- |
| Aspartic acid | $4.4\ 10^{-2}$ | $4.4\ 10^{-2}$ |
| Threonine | 5.6 " | 5.7 " |
| Serine | 9.8 " | 9.7 " |
| Glutamic acid | 10.3 " | 10.1 " |
| Proline | 6.1 " | 6.3 " |
| Glycine | 4.7 " | 5.1 " |
| Alanine | 3.4 " | 3.6 " |
| Aminoacids derived from the cystine group | 12.8 " | 12.6 " |
| Valine | 4.4 " | 4.5 " |
| Methionine | 0.3 " | 0.3 " |
| Isoleucine | 2.1 " | 2.1 " |
| Leucine | 5.0 " | 5.2 " |
| Tyrosine | 1.4 " | 1.2 " |
| Phenylalanine | 1.6 " | 1.6 " |
| Lysine | 2.0 " | 2.0 " |
| Histidine | 0.6 " | 0.6 " |
| Arginine | 5.2 " | 5.1 " |

According to another characteristic of the keratin polymer according to the invention, it generally contains from 2 to 5 S-sulphocysteine residues per peptide chain. In fact, as described in detail below, in the first step of the preparation of the polymer according to the invention, substantially all the intra-chain and inter-chain cystine linkages are converted to S-sulphocysteine residues. Furthermore, knowing on the one hand that the keratin used in the preparation of the polymer according to the invention can contain about 15 cystine residues on a chain of 100 amino acids (this being the case of hair), and on the other hand that the main fraction of the keratin polymer is composed of peptides having an average of 12 to 35 amino acids, it can be seen that the peptides constituting the main fraction of the keratin polymer according to the invention contain an average of about 2 to 5 S-sulphocysteine residues per chain.

Because of the fact that, in the preparation of the polymer according to the invention, virtually all the crystine linkages of the peptide chains of the starting keratin are converted to S-sulphocysteine residues, another characteristic of the polymer according to the invention is that it contains substantially no cysteine. This characteristic has been verified using the method described in SOKOL et al, J Soc Cosm Chem 25, 461 (1974).

The polymer according to the invention can be presented in the form of a dry residue obtained by lyophilisation or evaporation of the solvent medium. It can also be presented in the form of an aqueous solution with a pH of at least 7. Below pH 7, the peptide chains of the polymer precipitate, but redissolve when the pH becomes alkaline again. On drying, the keratin polymer according to the invention spreads out in the form of a thin film-forming layer, which can be broken up to form shiny flakes.

The present invention also provides a process for the preparation of a polymer of this invention from keratin substances, characterised in that, firstly, substantially all the cystine linkages between the peptide chains of the starting keratin substance are converted to S-sulphocysteine residues, substantially without forming cysteine residues, the said conversion being carried out by oxidising sulphitolysis in the presence of, say, copper or thionate(s), and in that, secondly, enzymatic digestion of the keratin substance treated in this way is carried out in a manner which is in itself known.

It is known that the sulphitolysis reaction of keratocystine is the following equilibrium reaction (in which "Ker" represents a peptide chain of the keratin):

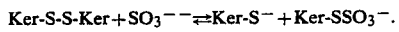

$Ker\text{-}S\text{-}S\text{-}Ker + SO_3^{--} \rightleftharpoons Ker\text{-}S^- + Ker\text{-}SSO_3^-$.

To displace the equilibrium of the above-mentioned reaction towards the right, so as to convert the cystine residues to S-sulphocysteine residues ($Ker\text{-}SSO_3^-$), and also in order to prevent the formation of cysteine residues ($Ker\text{-}S^-$), the starting keratin is treated by oxidising sulphitolysis. Amongst the various techniques of oxidising sulphitolysis which can be used in the process according to the invention, there may be mentioned, in particular, the sulphitolysis in the presence of copper, in an ammoniacal medium at pH 9, described by I M KOLTHOFF and W STRICKS, J Amer Chem Soc, 73, 1728 (1951), the disclosure of which is hereby incorporated by reference. This sulphitolysis reaction can be represented as follows: $Ker\text{-}S\text{-}S\text{-}Ker + 2SO_3^{--} + Cu^{++} \rightarrow 2Ker\text{-}SSO_3^- + 2Cu^{++}$. It is also possible to conduct the oxidising sulphitolysis in the presence of thionate(s) as described by J L BAILEY, Biochem, J 64–21 P (1957), the disclosure of which is hereby incorporated by reference. The sulphitolysis reaction in the presence of tetrathionate(s) can be represented by the following equation: $Ker\text{-}S\text{-}S\text{-}Ker + 2SO_3^{--} + S_4O_6^{--} \rightarrow 2Ker\text{-}SSO_3^- + 2S_2O_3^{--}$.

In the process according to the invention, it is preferred to use oxidising sulphitolysis in the presence of trithionate. The trithionate is advantageously prepared by bubbling sulphur dioxide into a solution of thiosulphate. After removal of the precipitate of sulphur formed, the trithionate solution is brought into contact with the keratin substances to be sulphitolysed, in the presence of thiosulphate and sulphite. The two reactions for the preparation of a solution of trithionate and for the sulphitolysis of the crystine in the presence of trithionate can be prepared by the following scheme:

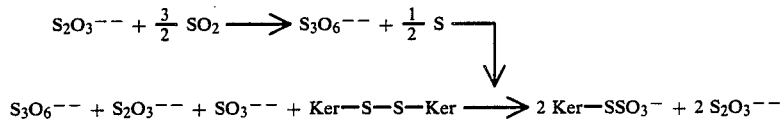

$S_2O_3^{--} + \frac{3}{2} SO_2 \longrightarrow S_3O_6^{--} + \frac{1}{2} S$ $S_3O_6^{--} + S_2O_3^{--} + SO_3^{--} + Ker\text{-}S\text{-}S\text{-}Ker \longrightarrow 2\,Ker\text{-}SSO_3^- + 2\,S_2O_3^{--}$ From the practical point of view, the oxidising sulphitolysis should be completed by copious washing of the keratin materials treated, so as to remove the reactants. In the case of sulphitolysis in the presence of copper, this washing must be particularly thorough: it is generally necessary to immerse the sulphitolysed keratin substances firstly in normal hydrochloric acid at 40° C. for 16 hours, and then in an equal volume of normal hydrochloric acid at ambient temperature for 24 hours. On the other hand, in the case of keratin substances treated by oxidising sulphitolysis in the presence of trithionate, it is simply necessary to wash them copiously with water.

The second step of the process according to the invention consists in carrying out enzymatic digestion of known type on the keratin substances treated by oxidising sulphitolysis, with the aid of, say, a proteolytic enzyme (such as proteinase "PSF 2019", pronase, trypsin or papain). The conditions of the enzymatic digestion, such as the pH and the enzyme/substrate ratio, naturally depend on the enzyme used.

It has been found, surprisingly, that, compared with enzymatic digestion carried out in a conventional manner on keratin fibres, on the one hand the rate of enzymatic digestion in the second step of the process according to the invention, and on the other hand the extent of digestion, are substantially increased by virtue of the pretreatment of the keratin fibres by oxidising sulphitolysis.

Thus, the extent of enzymatic digestion has been compared for:

(a) natural hair;

(b) the same natural hair subjected beforehand to sulphitolysis of a conventional type, with partial reduction of the cystine to cysteine and formation of an equivalent amount of S-sulphocysteine (as described in the article by KUNERT, ZEITSCHRIFT FUR ALLG. MIKROBIOLOGIE, volume 16, No 2 (1976)); and (c) the same natural hair treated by means of oxidising sulphitolysis in the presence of copper (in accordance with the procedure described in Example 1 below).

Instead of being subjected to enzymatic digestion, a fraction of the sulphitolysed hair mentioned under (c) above was simply immersed in an aqueous solution at the same pH, and the degree of solubilisation of this fraction of hair (d) calculated. The fractions of hair (a), (b) and (c) above were subjected to enzymatic digestion carried out under the same conditions, in particular as regards the pH, the temperature and the enzyme used. Similar results to those obtained by means of oxidising sulphitolysis in the presence of copper were obtained when oxidising sulphitolysis was carried out in the presence of thionate (in accordance with the procedure described in Example 3 below) (see lines e and f of the following table). The conditions and results of these comparative experiments are summarised in the following table:

| | | |
|---|---|---|
| (a) natural hair | digestion with proteinase "PSF 2019" pH 9 - 24 hours - 30° C. | extent of digestion ≃ 5% |
| (b) sulphitolysed hair | digestion with proteinase "PSF 2019" pH 9 - 24 hours - 30° C. | extent of digestion ≃ 15% |
| (c) hair sulphitolysed in the presence of copper (Example 1) | digestion with proteinase "PSF 2019" pH 9 - 2 hours - 30° C. | extent of digestion ≃ 100% |
| (d) hair sulphitolysed in the presence | immersion in an aqueous solution pH 9 (without en- | degree of solubilisation ≃ 2% |

| | | |
|---|---|---|
| of copper (Example 1, 1st step) | zyme) - 24 hours - 30° C. | |
| (e) hair sulphi- tolysed in the presence of trithio- nate (Example 3) | digestion with pro- teinase "PSF 2019" pH 9 - 2 hours - 30° C. | extent of diges- tion ≃ 100% |
| (f) hair sulphi- tolysed in the presence of trithio- nate (Example 3, 1st step) | immersion in an aqueous solution pH 9 (without en- zyme) - 24 hours - 30° C. | degree of solubi- lisation ≃ 2% |

The table above clearly shows that the extent of digestion is considerably increased when the keratin fibres are subjected to a pretreatment of oxidising sulphitolysis in the presence of copper of thionate(s).

It is important to note that the enzymatic digestion has virtually no effect on the proportion of S-sulphocysteine residues formed during the oxidising sulphitolysis. Thus, for the polymer prepared in accordance with the procedure described in Example 3 below, and for the initial hair used for the preparation of this polymer, a quantitative analysis of the cysteine and sulphocysteine groups was carried out in accordance with the above-mentioned method described by SOKOL et al. The results of this analysis are summarised in the table below.

| | CYSTEINE | S-SULPHOCYSTEINE |
|---|---|---|
| Initial fraction of hair | 0 | 0 |
| Fraction of hair sulphi- tolysed in the presence of trithionate (accord- ing to Example 3, 1st step) | 0 | 1.10 milliequi- valents/g |
| Keratin polymer ob- tained according to Example 3 | 0 | 1.08 milliequi- valents/g |

The present invention also provides a cosmetic composition for treating the hair or skin, the said composition being characterised in that it contains, in a cosmetically acceptable carrier, an effective amount of at least one keratin polymer of this invention.

In fact, like all protein hydrolysates, the keratin polymer according to the invention has an affinity for the skin and keratin fibres because of the presence of free carboxyl and amine end groups at both ends of the peptide chains, which are capable of forming a large number of ionic linkages with the complementary groups of the proteins to be treated.

However, the keratin polymer of the invention has a much greater affinity towards reduced keratin fibres, since the S-sulphocysteine groups of the polymer (ker-S-SO$_3^-$, in which "ker" represents a peptide sequence resulting from the fractionation of the long peptide chains of a keratin by enzymatic hydrolysis react with the cysteine groups (Cys-S$^-$) according to the following equilibrium reation:

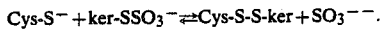

$$Cys\text{-}S^- + ker\text{-}SSO_3^- \rightleftharpoons Cys\text{-}S\text{-}S\text{-}ker + SO_3^{--}.$$

The reaction involving fixing of the cysteine by the peptides containing S-sulphocysteine groups of the polymer according to the invention is the reverse reaction of the sulphitolysis of the keratin fibres. The reaction equilibrium can be displaced towards the right if the keratin polymer is used in excess relative to the cysteine of the reduced keratin fibre.

Furthermore, as the peptides which constitute the main fraction of the keratin polymer contain from 2 to 5 S-sulphocysteine residues per chain, it can be seen that the fixing of the keratin polymer to the reduced fibres is accompanied by the creation of bridge linkages between the peptide chains of the reduced keratin fibres, with, moreover, an excess of reactive acid groups —S-SO$_3^-$. The fixing of the polymer to the reduced keratin fibres can be represented by the following equation:

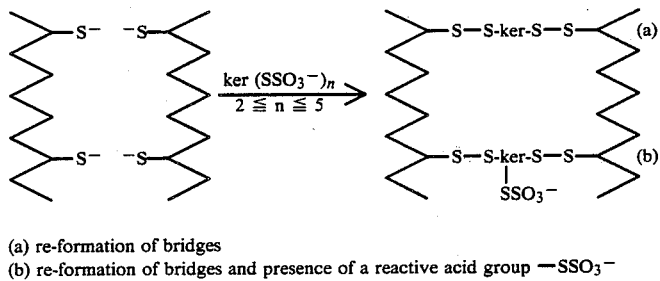

(a) re-formation of bridges
(b) re-formation of bridges and presence of a reactive acid group —SSO$_3^-$ The "ker" group of the polymer [ker(SSO$_3^-$)$_n$] represents a peptide sequence having a molecular weight of, say, 1,100 to 7,500 resulting from the fractionation of the long peptide chains of the keratin by enzymatic hydrolysis.

Thus, it has been observed that the fixing of the polymer according to the invention to the reduced keratin fibres has the effect of re-forming the disulphide bridges and of enriching the hair in keratin, while at the same time leaving behind reactive acid groups —SSO$_3^-$ which can be used for the fixing of, for example, basic dyestuffs, cationic compounds or alternatively one or more other cysteine radicals, the reaction thus resulting in a true crosslinking of the hair.

For the treatment of reduced keratin fibres, in particular hair, the treating composition used suitable contains from 1 to 10%, and preferably from 3 to 6%, by weight, of keratin polymer(s) and has a pH of at least 7 and preferably a pH of 9 to 10.

We have shown that if one mol of cysteine and 10 equivalents of

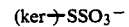

$$(ker \rightarrow SSO_3^-$$

are brought into contact at a temperature of, say, 30° C. for 30 minutes at pH 9, the cysteine is "fixed" to the extent of 95% (a cysteine control at pH 9 under the same conditions, but in the absence of keratin polymer, shows a conversion of cysteine to cystine of less than 15%).

By analysing various reduced keratins treated with a treating composition according to the invention (containing 3% by weight of keratin polymer in solution at pH 9), we have also been able to show that the cysteine initially present in the keratin fibres disappears with time and with the number of applications.

Thus, if a fraction of hair is treated with a reducing liquid for soft perming, analysis shows the presence of 2% (by weight) of cysteine. The fraction of reduced hair is washed in order to remove the excess reducing agent; it is then treated at, say, 30+ C. with the 3% strength solution of a keratin polymer according to the invention (at pH 9). The immersion operations last 15 minutes. The hair is then towel-dried and dried at 50° C. under a hood. The application of the polymer solution is repeated five times. After the third and fifth applications, the hair is rinsed with water before being dried. The proportion of cysteine in the hair during these applications is given in the following table:

|  | Initial fraction of hair | After the 1st application | After the 2nd application | After the 3rd application | After the 4th application | After the 5th application |
|---|---|---|---|---|---|---|
| Proportion of cysteine | 2% | 1.1% | 0.8% | 0.6% | 0.5% | 0.4% |

The keratin fibres treated with the treating composition according to the invention become reactive themselves as a result of the excess S-sullphocysteine groups which remain free. The treated hair can therefore react by covalent bonding with thiols or by ionic attraction with basic dyestuffs and with cationic molecules such as trimethylcetylammonium bromide marketed under the name "Cetavlon" by ICI, or reactive polymers of the "ionene" type, such as those described in French Patents Nos. 2,333,012, 2,270,846, 2,316,271, 2,331,323, 2,331,324, 2,471,996, 2,471,776, 2,471,997 and 2,471,777. The new keratin polymer can be used as a so-called "A.P." type molecule (anionic polymer) for reaction with a molecule of the so-called "C" type (simple cationic molecule) (see JK 80 145608, 80 115813; French Patent No. 2,237,616; U.S. Pat. Nos. 4,247,538 and 4,210,161) or with a molecule of the called "C.P." type (cationic polymer) (see French Patents Nos. 2,383,660 and 2,436,213) in order to impart valuable properties to the keratin fibres.

The following Examples further illustrate the present invention.

EXAMPLE 1

First Step (a) oxidising sulphitolysis in the presence of copper 100 g of hair cut to a length of about 2 cm are immersed in a solution containing:

| Anhydrous Na$_2$SO$_3$ | 350 g |
|---|---|
| CuCl$_2$.2H$_2$O | 30 g |
| NH$_4$OH q.s. | pH 9 |
| H$_2$O q.s. | 3.5 l |
| The immersion lasts for 24 hours at 40° C. | |

(b) washing

The treated hair is washed copiously with water; it is subsequently immersed for 16 hours in normal HCl at 40° C. and then for 24 hours in normal HCl at ambient temperature. Just before enzymatic digestion, it is rinsed with water until the solution is neutral.

Second step: Enzymatic digestion

An enzymatic solution containing 1.7 g of proteinase "PSF 2019" (11,000 AU per mg, sold by ORIL, Paris) is 3 liters of water is brought to pH 9 with aqueous ammonia solution; the sulphitolysed hair is added gradually to the enzyme solution. The hair is agitated continuously and the suspension is kept at a temperature of 40° C.

Every 15 minutes, the pH is readjusted to 9 with NH$_4$OH. After one hour, when about half of the hair has been brought into contact with the enzyme solution, a further 1.7 g of proteinase "PSF 2019" are added.

After 3 hours (from the start of the digestion operation), virtually all the hair has been digested.

The solution can be filtered on gauze in order to remove the residues of undigested fibres. The solution is lyophilised.

A blackish power is obtained. The colour is due to the melanic pigments in the starting hair.

The results obtained are as follows:

| Extent of digestion | ≃ 100% |
|---|---|
| Initial proportion of ½ cystine | 1.17 milliequivalent of protein substance |
| Proportion of S-sulphocysteine groups | 0.94 milliequivalent/g of protein substance. |

EXAMPLE 2

First Step (a) oxidising sulphitolysis in the presence of copper

The same solution is used as in Example 1 (a) mentioned above.

Immersion in the solution sulphite/cupric chloride solution lasts for 4 hours at 60° C. The hair is agitated regularly.

(b) washing

The same procedure is followed as in Example 1 (b).

Second Step: Enzymatic digestion

An enzyme solution containing 7.5 g of trypsin "TPCK" (217 AU/mg) in 4 liters of water is brought to pH 8 with aqueous ammonia solution.

The sulphitolysed hair added gradually to the enzyme solution. The hair is aggitated continuously and the suspension is kept at a temperature of 40° C.

Every 15 minutes, the pH is readjusted to 8 with NH$_4$OH. After one hour, when about 50 g of hair has been brought into contact with the enzyme solution, a further 7.5 g of trypsin are added.

After 3 hours (from the start of the digestion operation), virtually all the hair has been digested. The solution is lyophilised.

This gives a powder similar to that obtained in Example 1. The extent of digestion is about 100%.

EXAMPLE 3

First Step (a) oxidising sulphitolysis in the presence of trithionate 348 g of sodium thiosulphate ($Na_2S_2O_3.5H_2O$) are dissolved in 3 liters of water. $SO_2$ is bubbled at a rate of about 40 g per hour.

The solution becomes turbid and turns yellow and a precipitate of sulphur appears. The $SO_2$ is allowed to evolve for 3 hours.

The precipitated sulphur is then filtered off.

A further 348 g of sodium thiosulphate are added to the solution, followed by 265 g of sodium sulphite (anhydrous $Na_2SO_3$).

The pH is adjusted to 6.5 and the total volume is made up to 3.5 liters with water.

100 g of hair cut to a length of about 2 cm are immersed in this solution, which is kept at 40° C. for 15 hours.

(b) washing

The treated hair is washed copiously with four times 5 liters of water.

Second Step: Enzymatic digestion

The same enzyme solution is used as in Example 1.

A black solution is obtained, which is lyophilised. The results obtained are as follows:

| | |
|---|---|
| Extent of digestion | ≃ 100% |
| Initial proportion of ½ cystine | 1.17 milliequivalents/g of protein substance. |
| Proportion of S-sulphocysteine groups | 1.08 milliequivalents/g of protein substance. |

EXAMPLE 4

First Step (a) oxidising sulphitolysis in the presence of trithionate

The same solution is used as in Example 3 (a) mentioned above.

100 g of yak hair cut to a length of about 2 cm are immersed in this solution, which is kept at 40° C. for 7 hours.

(b) washing

The treated yak hair is washed copiously with four times 5 liters of water.

Second Step: Enzymatic Digestion

An enzyme solution containing 1.3 g of pronase in 3 liters of water is brought to pH 9 with aqueous ammonia solution. The sulphitolysed yak hair is added gradually to the enzyme solution. The hair is agitated continuously and the suspension is kept at a temperature of 40° C.

Every 15 minutes, the pH is readjusted to 9 with $NH_4OH$.

After one hour, when about 50 g of hair has been added to the enzyme solution, a further 1.3 g of pronase are added.

After 3 hours (from the start of the digestion operation), virtually all the hair has been digested.

The solution is lyophilised. A white powder is obtained.

The results obtained are as follows:

| | |
|---|---|
| Extent of digestion | ≃ 100% |
| Initial proportion of ½ cystine | 0.83 milliequivalents/g of protein substance. |
| Proportion of S-sulphocysteine groups | 0.67 milliequivalents of protein substance. |

EXAMPLE 5

First Step (a) oxidising sulphitolysis in the presence of trithionate 100 g of cut wool are immersed in a solution containing:

| | |
|---|---|
| $NaHSO_3$ in aqueous solution (specific gravity = 1.32) | 712 cm³ |
| Sodium trithionate | 833 g |
| $NH_4OH$ q.s. | pH 9 |
| $H_2O$ q.s. | 3.5 litres |

The immersion lasts for 15 hours at 40° C.

(b) washing

The treated wool is washed copiously with four times 5 liters of water.

Second Step: Enzymatic Digestion

An enzyme solution containing 7.5 g of trypsin "TPCK" (217 AU/mg) in 4 liters of water (the same enzyme solution as in Example 2) is brought to pH 8 with aqueous ammonia solution. The sulpholysed wool is added gradually to the enzyme solution. The wool is agitated continuously and the suspension is kept at a temperature of 40° C.

Every 15 minutes, the pH is readjusted to 8 with $NH_4OH$. After one hour, about 50 g of wool has been digested; a further 7.5 g of trypsin are then added.

After 3 hours (from the start of the digestion operation), virtually all the wool has been digested.

The solution is lyophlised. A white powder is obtained.

The results obtained are as follows:

| | |
|---|---|
| Extent of digestion | ≃ 100% |
| Initial proportion of ½ cystine | 0.70 milliequivalents/g of protein substance. |
| Proportion of S-sulphocysteine groups | 0.53 milliequivalents/g of protein substance. |

EXAMPLE 6

First Step (a) oxidising sulphitolysis in the presence of trithionate

The same solution is used as in Example 3 (a) mentioned above.

100 g of red chicken feathers are immersed in this solution, which is kept at 40° C. for 15 hours.

(b) washing

The treated feathers are washed copiously with four times 5 liters of water.

Second Step: Enzymatic Digestion

The same enzyme solution is used as in Example 1 (proteinase "PSF 2019").

The digestion lasts for 3 hours at 40° C., with agitation, the pH being readadjusted to 9 every 15 minutes.

After 3 hours, virtually all the feathers have been digested. The solution is filtered on gauze in order to remove the residues of indigested feathers. A reddish solution is obtained, which is lyophilised. The powder obtained is brown.

The results obtained are as follows:

| Extent of digestion | ≃ 90% |
|---|---|
| Initial proportion of ½ cystine | 0.58 milliequivalent/g of protein substance. |
| Proportion of S-sulphocysteine groups | 0.48 milliequivalent/g of protein substance. |

EXAMPLE 7

First Step (a) oxidising sulphitolysis in the presence of trithionate

The same solution is used as in Example 3 (a) mentioned above.

100 g of powdered horn, washed and degreased, are immersed in this solution, which is kept at 40° C. for 10 hours.

(b) washing

The powdered horn is washed with several liters of water.

Second Step: Enzymatic Digestion

The same enzyme solution is used as in Example 4 (pronase).

The digestion is continued for 3 hours at 40° C., with agitation, the pH being readjusted to 9 every 15 minutes.

After 3 hours, the solution is centrifuged in order to remove the undigested particles of horn. The supernatant solution can be lyophilised.

The results obtained are as follows:

| Extent of digestion | ≃ 75% |
|---|---|
| Initial proportion of ½ cystine | 0.42 milliequivalent/g of protein substance. |
| Proportion of S-sulphocysteine groups | 0.35 milliequivalent/g of protein substance. |

EXAMPLE 8

Improvement to the Take-up of Basic Dyestuffs on Pieces of Untreated Wool Fabric Pieces of untreated wool fabric (5×4 cm) are treated by immersion for 1 hour at 40° C. in a bath containing 4% of keratin polymer prepared according to Example 3, at pH 9.

The pieces of fabric are removed from the baths and rinsed with running water. They are then immersed for 30 seconds in baths containing various dyestuff molecules, at pH 9, in an exclusively aqueous medium.

They are squeezed between two sheets of filter paper and dried for 10 minutes at 110° C.

By way of comparison, pieces of fabric were treated, before dyeing under the same conditions, on the one hand with an aqueous solution at pH 9 (NH$_4$OH) and on the other hand with a 4% strength solution of a commercial keratin hydrolysate not containing S-sulphocysteine groups.

The dyestuffs used are as follows:
Methylene blue (CI52015)
Deorline brilliant red 3B (CI 42500)

The intensity of the colorations is compared by a group of observers: it is noted that the pieces of fabric treated with the polymer according to the invention have taken up the dye considerably better than the others.

EXAMPLE 9

Improvement to the Take-up of Basic Dyestuffs on Pieces of Reduced Wool Fabric Pieces of wool fabric (5×4 cm) are treated by immersion at 40° C. for 1 hour, either in a bath containing 0.1 mol/liter of thioglycolic acid at pH 9, or in a bath containing 1 mol/liter of ammonium sulphite at pH 7.

The pieces of fabric are removed from the baths and washed copiously with water.

The washed pieces of fabric are then treated by immersion for 1 hour at 40° C. in a bath containing 4% of keratin polymer prepared according Example 4, at pH 9.

The pieces of fabric are removed from the baths and washed with running water. They are squeezed between two sheets of filter paper and are then immersed for 30 seconds in baths containing various dyestuff molecules at pH 9 in an aqueous medium.

They are squeezed and dried at 110° C. for 10 minutes. By way of comparison, pieces of fabric were treated, after reduction and before dyeing under the same conditions, on the one hand with an aqueous solution at pH 9 (NH$_4$OH) and on the other hand with a 4% strength solution of a commercial keratin hydrolysate not containing S-sulphocysteine groups.

The dyestuffs used are as follows:
Deorline brilliant red 4G (CI 48013)
Deorline brilliant red 3B (CI 42500)
Astrazon blue B (CI 42140)
Methylene blue (CI 52015)

The intensity of the colorations is compared by a group of observers: it is noted that the pieces of fabric treated with the polymer according to the invention have fixed the dyes much better than the others. Furthermore, these pieces of fabric are more intensely coloured than those described in Example 8.

EXAMPLE 10

Improvement to the Take-up of Basic Dyestuffs on Reduced Wool Fibres

Untreated wool in the form of fibres (non-woven) is immersed for one hour at 40° C. in a reducing bath containing 0.1 mol/liter at thioglycolic acid at pH 9 (NH$_4$OH). The wool is removed from the reducing bath; it is washed very carefully with a large amount of water.

The reduced wool is immersed for 1 hour at 40° C. in a bath containing 4% of keratin polymer prepared according to Example 3, at pH 9.

The treated wool is removed from the bath and then washed with water.

It is then immersed for 30 seconds in baths containing basic dyestuff molecules at pH 9 in an aqueous medium.

The wool is squeezed and then dried at 110° C. for 30 minutes.

By way of comparison, wool fibres were treated, before dyeing and after reduction under the same conditions, with an aqueous solution at pH 9 (NH₄OH).

The dyestuffs used are as follows:
Deorline brilliant red 3B (CI 42500)
Methylene blue (CI 52015)

The intensity of the colorations is compared by a group of observers: it is noted that the wool treated with the polymer according to the invention is dyed much more homogeneously and that the intensity of the coloration is greater than that of the other wool samples.

EXAMPLE 11

Modification of the Coloration of Hair by Means of Basic Dyestuffs

Three solutions, (a), (b) and (c), are prepared for treating natural hair in order to impart a temporary coloration:

Pretreatment solution (a) has the following composition:

| | |
|---|---|
| pure thioglycolic acid (depending on the final intensity of coloration desired) | 0.30 g to 0.0090 g |
| NH₄OH q.s. | pH 9 |
| perfume | 0.1 g |
| water q.s. | 100 cm³ |

Treatment solution (b) has the following composition:

| | |
|---|---|
| keratin polymer (according to one of the examples described) | 5 g |
| NH₄OH q.s. | pH 9 |
| perfume | 0.1 g |
| water q.s. | 100 cm³ |

Colouring solution (c) has the following composition:

| | |
|---|---|
| basic dyestuff (for example: methylene blue, deorline red 3G or astrazon blue B) | 0.1 g |
| NH₄OH q.s. | pH 9 |
| perfume | 0.1 g |
| water q.s. | 100 cm³ |

Grey hair is treated with pretreatment solution (a) for 20 minutes at 30° C. It is then washed with water. The treatment with solution (b) lasts for 15 minutes at 30° C. Without washing the hair, colouring solution (c) is applied for a few seconds.

The hair is then rinsed copiouslsy with hot water (45° C.) and dried under a hood.

The hair appears very distinctly coloured.

If treatment solution (b) is replaced by a solution containing 5% of a keratin hydrolysate (rich in cystine) at pH 9, or 5% of gelatin at pH 9, or an aqueous solution at pH 9 (not containing the protein derivative), the hair then appears only very slightly coloured.

Likewise, the control hair treated directly with colouring solution (c) took up the dyestuffs to only a very small extent.

We claim:

1. A process for preparing a polymeric product comprising keratin peptide chains of different molecular weight, said peptide chains being formed of amino acids bonded to one another by amide groups, the amino acid composition of said polymeric product being substantially identical to the amino acid composition of the keratin substance from which said polymeric product is prepared, more than 75 percent of the cysteine linkages of said peptide chains being in the form of S-sulphocysteine, said peptide chains terminating at one end in a free carboxyl group and at their other end in a free amine group, the major part of said peptide chains having a molecular weight from about 1,100 to about 7,500,
    said process comprising converting substantially all the cysteine linkages between the peptide chains of a keratin substance to S-sulphocysteine residues, substantially without forming cysteine residues, by oxidizing sulphitolysis with an aqueous solution of sulfite containing copper or a thionate and enzymatically digesting the resulting keratin substance.

2. Process according to claim 1 in which the thionate used is a trithionate.

3. Process according to claim 2 in which the trithionate is prepared by bubbling sulphur dioxide into a solution of thiosulphate.

4. Process according to claim 1 in which the starting keratin substance is human hair, bristles, wool, animal hair, poultry feathers or horn.

5. The polymeric product produced by the process of claim 1.

* * * * *